US005876697A

United States Patent [19]

Soetanto

[11] Patent Number: 5,876,697

[45] Date of Patent: Mar. 2, 1999

[54] METHOD FOR THE PRODUCTION OF MICROBUBBLE-TYPE ULTRASONIC CONTRAST AGENT USING FATTY ACID SURFACTANTS

[75] Inventor: Kawan Soetanto, Yokohama, Japan

[73] Assignee: Gakko Houjin Toin Gakuen, Kanagawa, Japan

[21] Appl. No.: 509,942

[22] Filed: Aug. 1, 1995

[30] Foreign Application Priority Data

Aug. 4, 1994 [JP] Japan .................................... 6-183491

[51] Int. Cl.[6] ...................................................... A61K 49/04

[52] U.S. Cl. ................... 424/9.52; 424/9.51; 128/662.02

[58] Field of Search .................................... 424/9.52, 9.5, 424/9.51, 450, 489; 128/662.02

[56] References Cited

U.S. PATENT DOCUMENTS

| | | |
|---|---|---|
| 4,684,479 | 8/1987 | D'Arrigo . |
| 4,774,958 | 10/1988 | Feinstein . |
| 4,844,882 | 7/1989 | Widder et al. . |
| 4,983,045 | 1/1991 | Taniguchi . |
| 5,215,680 | 6/1993 | D'Arrigo . |
| 5,469,854 | 11/1995 | Unger et al. ....................... 128/662.02 |
| 5,487,390 | 1/1996 | Cohen et al. ...................... 128/662.02 |
| 5,518,709 | 5/1996 | Sutton et al. .......................... 424/9.52 |

FOREIGN PATENT DOCUMENTS

| | | |
|---|---|---|
| 0 324 938 A1 | 7/1989 | European Pat. Off. . |
| 0 365 467 A2 | 4/1990 | European Pat. Off. . |
| 0 447 297 A1 | 9/1991 | European Pat. Off. . |
| 0 467 031 A2 | 1/1992 | European Pat. Off. . |
| 0 556 957 A1 | 8/1993 | European Pat. Off. . |
| 61-21723 | 1/1986 | Japan . |
| 62-125836 | 6/1987 | Japan . |
| 63-44927 | 2/1988 | Japan . |
| 63-310630 | 12/1988 | Japan . |

OTHER PUBLICATIONS

Richard H. Simon et al., "Lipid–Coated Ultrastable Microbubbles As a Contrast Agent In Neurosono–graphy," Investigative Radiology, vol. 25, Dec. 1990, pp. 1300–1304.

Jonathan Ophir et al., "Contrast Agents in Diagnostic Ultrasound," Ultrasound In Medicine And Biology, vol. 15, No. 4, 1989, pp. 319–333.

S. Budavari (Editor), "Merck Index", *Merck & Co.,* 11th Edition, entry No. 8328, p. 1328, 1989.

James Reynolds et al. (Editors), "Martindale—The Extra Pharmacopoeia", *The Pharmaceutical Press,* 28th Edition, entry No. 470–r, p. 376, 1982.

James Reynolds et al. (Editors), "Martindale—The Extra Pharmacopoeia", *The Pharmaceutical Press,* 28th Edition, entry No. 6027–b, p. 1443, 1982.

H.J. Bleeker et al., "Ultrasonic Characterization of Albunex®, a New Contrast Agent", *J. Acoust. Soc. Am.,* vol. 87, No. 4, pp. 1792–1797, 1990.

Richard H. Simon, MD. et al., "Quantitative Assessment of Tumor Enhancement by Ultrastable Lipid–Coated Microbubbles as a Sonographic Contrast Agent", *Investigative Radiology,* vol. 27, No. 1, pp. 29–34, 1992.

Richard H. Simon, MD. et al., "Applications of Lipid–Coated Microbubble Ultrasonic Contrast to Tumor Therapy", *Ultrasound in Medicine and Biology,* vol. 19, No. 2, pp. 123–125, 1993.

N.de Jong et al., "Principles and Recent Developments in Ultrasound Contrast Agents", *Ultrasonics,* vol. 29, pp. 324–330, 1991.

N.de Jong et al., "Absorption and Scatter of Encapsulated Gas Filled Microsheres: Theoretical Considerations and Some Measurements", *Ultrasonics,* vol. 30, No. 2, pp. 95–102, 1992.

N.de Jong et al., "Ultrasound Scattering Properties of Albunex® Microspheres", *Ultrasonics,* vol. 31, No. 3, pp. 175–181, 1993.

*Primary Examiner*—Gary E. Hollinden
*Assistant Examiner*—Michael G. Hartley
*Attorney, Agent, or Firm*—Oliff & Berridge, PLC

[57] ABSTRACT

An imaging agent for ultrasound to be administered into a vein is provided. More specifically, an imaging agent for ultrasound containing microbubbles, which has a long-life and is stable within a human body even after is has passed through a lung, and a method for producing the same, are provided.

A method for producing an imaging agent for ultrasound comprises a mixing step wherein a mixture of water, Sodium Stearate, Saponin and $CaCl_2$ and gas are mixed by a homogenizer for forming bubbles, and a separation step wherein bubbles having a desired size are separated according to their buoyancy after the mixing step. The mixing step further includes two stages, i.e., a low speed mixing stage and a high speed mixing stage. In the low speed mixing stage, a shaft of the homogenizer is immersed into a solution containing a preset amount of Sodium Stearate, Saponin, and $CaCl_2$, which is mixed at a low rotation speed for a given period of time and is then left for a given period. Then, such a process is repeated. In the high speed mixing stage, said solution is mixed for a given period at a high rotaion speed. After this 2-stage mixing step, the separation is performed by using a burette, thereby obtaining microbubbles of a desired size.

13 Claims, 5 Drawing Sheets

METHOD FOR THE PRODUCTION OF MICROBUBBLE-TYPE ULTRASONIC CONTRAST AGENT USING FATTY ACID SURFACTANTS

FIELD OF INVENTION

This invention relates to method for the production of long-life stable, uniformly small size microbubbles which has the potential to be useful as a contrast agent in ultrasonic imaging.

BACKGROUND OF INVENTION

Various technologies exist in which parts of an animal or human body may be images so as to aid in diagnosis and therapy of medical disorders. Some of these existing techniques are described in this section.

X-ray is the most well-known imaging techniques to visualize skeletal and other internal structures within animals and humans. However, a number of problems associates with the use of X-rays. Firstly, X-ray is not a safe diagnostic method is visualizing some parts of the human body, the use of X-ray for some of the organs and blood vessels is unsatisfactory. In addition, X-ray is dangerous if the amount of exposure is excessive; further, all X-ray radiation absorbed over a lifetime is cumulative.

Another technique, radio-nuclide imaging involves the injection of radioactive substances, such as thallium into the bloodstream. This technique require the use of very expensive and sophisticated machinery. Further, radionuclide imaging produces images of only a limited number of view of the heart and those images may not be of exceptional clarity. Finally, this type of radiation is cumulative over a lifetime and this is hazardous.

Ultrasound imaging techniques is safe, cheap, relatively easy to operate and the image produced is in real-time. Therefore, ultrasound is widely used in diagnostic imaging nowadays. The basis for ultrasound imaging is that, ultrasonic waves are sent into human body by an ultrasound probe and the waves reflected from the tissues are detected by the same probe, the receive signal is then processed to produce images on a monitor by a ultrasonic diagnostic instrument. According to different acoustic properties of different tissues in the human body, the diagnosis of diseased tissues can be distinguished from normal tissues quickly by observing the real-time image produced on the monitor. In addition to diagnostic application, the visualization of blood flow is also a common application of ultrasound in medical imaging, by monitoring the change in frequency of ultrasonic waves sent to blood vessels and the reflected waves. The blood flow velocity can be calculated.

Since early ultrasound techniques suffered from a lack of clarity, extensive efforts were undertaken to improve the ultrasonic equipment. To deal with this problem, it is valuable to mention that when ultrasonic energy is directed through substances, changes in the substances' acoustic properties will be most prominent at the interface of different media (i.e. solids, liquids and gases). As a consequence, when ultrasound energy is directed through various media, the reflection of ultrasound at the interface of different media will be the strongest and can be detected most easily. That is the basic principle for the making of ultrasonic contrast agents.

Contrast agents were introduced into the bloodstream in an effort to obtain enhanced images. The maximum ultrasonic reflection that we can obtain is that from the interface between liquid and gaseous media. That is way many of these contrast agents were liquids containing microbubbles of gas. These contrast agents themselves are intense sound wave reflectors because of acoustic differences between the liquids and the gas microbubbles enclosed therein. When the contrast agents are injected into and perfuse the microvasculative to tissue, clearer images of such tissue may be produced. However, not withstanding the use of such contrast agents, the image produced, for example, of the myocardial tissue, is of relatively poor quality, is highly variable and is not quantifiable due to the variable size and persistence associated with prior art microbubbles.

In the recent years, much effort was made to manufacture microbubble type contrast agents which includes Albunex® by Widder et al and Lipid-Coated Microbubbles (LCM) by D'Arrigo. For the commercially existing ultrasonic contrast agent Albunex®, although has a reported mean diameter under 6 μm, up to 0.5% of the microbubbles, or up to 2,000,000 microbubbles/ml are over 9 μm in diameter in the fully purified product. According to J. Ophir, the microbubbles which are above 3 to 5 μm will not pass through the lung capillaries. Therefore, the microbubbles cannot reach the organs to provide diagnostic properties. In this sense, microbubbles sized below 5 μm should be made in order to overcome this problem. Overcoming the problem of size, D'Arrigo successfully made Lipid-Coated Microbubbles (LCM) of which 99% of the microbubbles are sized below 4.5 μm in diameter by the use of surfactants. However, the number of microbubbles made in D'Arrigo's invention is much less than that of Albunex® which is in the order of $1\times10^8$. The number of microbubbles made by D'Arrigo is in the order of $1\times10^6$. For the best imaging properties to occur, it is desirable to have higher concentration of microbubbles. Furthermore, there is not yet a method or a effective way to control the size of the microbubbles produced which may suit different conditions for other commercial uses.

SUMMARY OF INVENTION

This invention is directed to an improvement associated with producing microbubble type ultrasonic contrast agent by which large concentration of small and uniform size of microbubbles are produced in water base. A second embodiment is directed to the method to control the size of microbubbles produced in order to suit different situations.

The present invention is directed to methods to produce large concentration, room temperature stable microbubble type contrast agents which involves procedures which is capable of producing microbubbles with the size range from less than 1 μm to 200 μm, and then microbubbles of different sizes can be collected easily within this size range.

The ultrasonic contrast agents in the present invention are microbubbles of the following properties (i) ultrasonically echogenic (i.e. capable of reflecting sound waves).

(ii) uniform size and small enough to pass through lung capillary system, thereby producing enhances image of various kinds of tissues and organs and permitting differentiation between well-perfused and poorly-perfused tissue.

(iii) quantifiably reproducible.

(iv) long-life for storage in vitro.

The basic components of this invention comprises (1) Homogenizer of which (a) the shaft can rotate at a speed (from 0 to about 20,000 rpm) and it can rapidly introduce bubbles into the solution in which the shaft is immersed in the liquid.

(b) has hole on the shaft which is capable of sucking air or gases from the outside environment. After the air is sucked from the outside, by the high-speed rotating motion, the air is rapidly introduced into the solution.

(c) the basic function is to make particle smaller by mechanical means.

In this invention, a new function of the homogenizer is introduced that the homogenizer can be used to produce microbubbles of smaller size range from 0.5 μm to 5 μm.

(2) a member chosen from the group of surfactants consisting of Sodium Salt of saturated carboxylic acids containing from about 10 to about 18 carbon atoms. Examples includes Sodium Stearate, Sodium Mystritate, Sodium Palmitate, Sodium Laurate, Sodium Oleate . . . etc.

(3) Another material chosen from the group of surfactants which is currently used as producing bubbles which includes (i) Saponin
(ii) Stearic acid
(iii) Phloxine
(iv) Crystal Violet
(v) Polyvinyl alcohol
(vi) Sodium Laurate which is capable of stabilizing microbubbles produced from surfactant described above in (2) temporarily and the other function is to slow down the rapid reaction between surfactant mentioned in (2) and the stabilizer that will be described immediately in point (4).

(4) a member chosen from the group of reagents which can change the nature of the surface of the microbubbles produced from the surfactants mentioned in point 2 above. These include the salts when dissolved in water, the cation come out will have a reaction which the group (2) and (3) mentioned above. Examples of these are Calcium Chloride and Magnesium Chloride.

(5) a separation procedure to enable us to collect different range of size of bubbles according to our interest.

Firstly a mixture is made by admixing solid selected from group (2) and (3) described above.

Said mixture from group (2) and (3) in the said ratio 1.0:0.1–1.0:2.0.

Said mixture is put into pure water to make a dilute solution. After the solution is made, to ensure that the surfactants are fully dispersed in the pure water and to produce a concentrated emulsion of microbubbles, a stepwise-homogenizing technique is used. That is, first the solution is homogenized at slower homogenizer speed for a short time, and repeat the above procedure once. Then a faster homogenizer speed and longer time of homogenizing is used to produce an emulsion which contains large amount of microbubbles. The main use of chemical mentioned in group (3) in this invention is to stabilize the microbubbles produced from group (2) for a short period of time before another stabilizer is added to stabilize the microbubbles produced. By controlling the procedure of homogenizing, such as homogenizing speed and time, we can control the size and amount of bubbles produced quantitatively.

Then the emulsion is put into a burette. Burette is a glass tube with a stopcock at the bottom. After the emulsion is put into the tube, because of the faster rising time of larger bubbles, different sizes of bubbles can be obtained at different levels of the burettes after a period of time.

By collecting the microbubbles at the bottom of the burette. We can obtain the microbubble of the smallest size which ranges from 0.5 μm to 5 μm.

After microbubbles are collected, a small amount of 0.2–30% of solution from group (4) is added into the bubble solution to change the nature of the coating produced by the surfactants. Thereby, stabilizing the bubble produced.

According to different purposes of usage, different sizes of bubbles can be obtained by carefully controlling the homogenizing speed and time, and the collection time and level. The microbubbles exists for at least 6 months after they are produced.

In this invention, the mean bubble diameter produced can be smaller than 0.5 μm and 99% of microbubble diameter is less than 3 μm.

BRIEF DESCRIPTION OF THE DRAWINGS

FIG. 5 are photographs showing the microbubbles observed by 600 times microscopy.

DETAILED DESCRIPTION OF THE INVENTION

Figure 1:
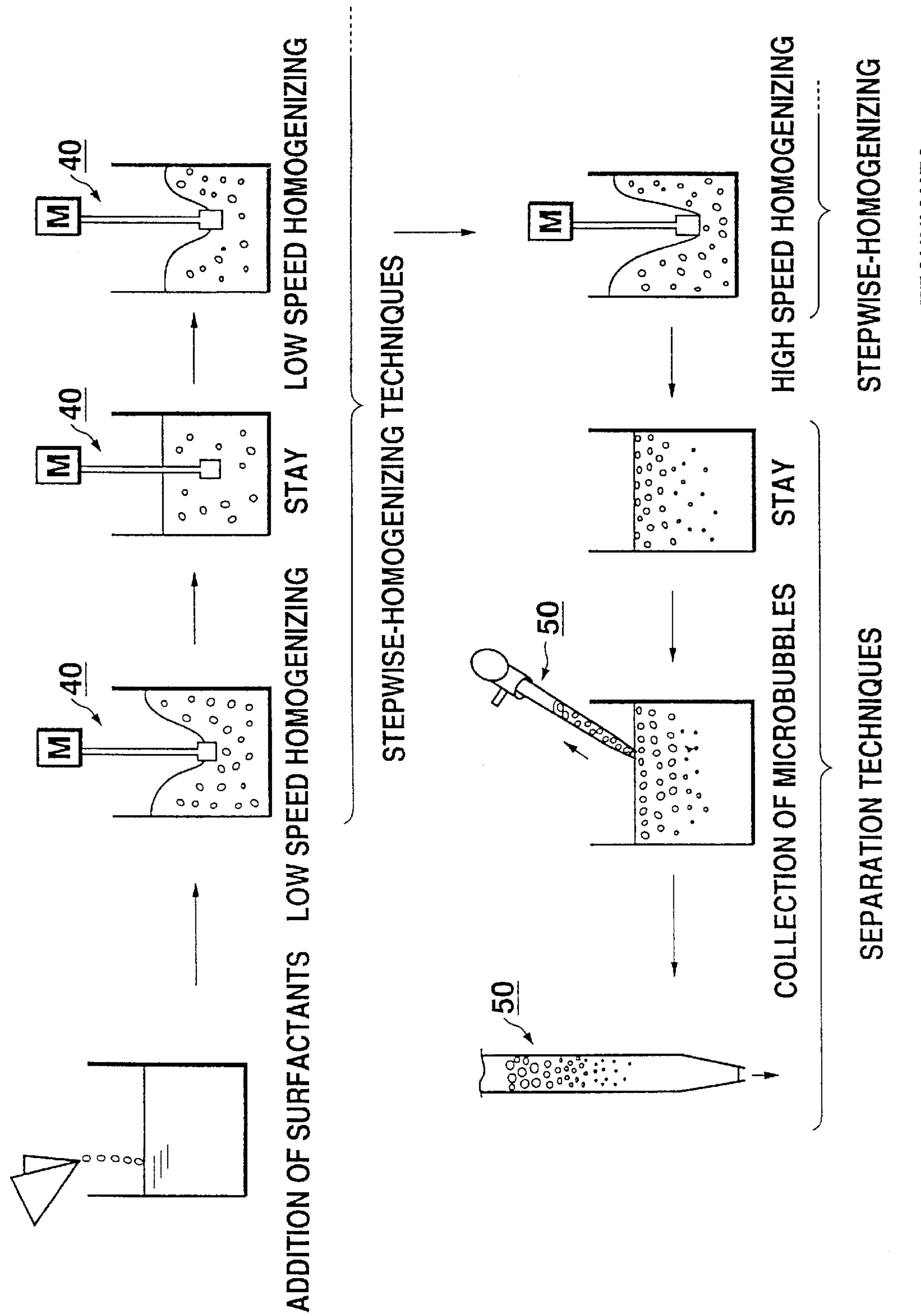
FIG. 1 is the graphically illustration of the method of production of microbubbles.
Figure 2:
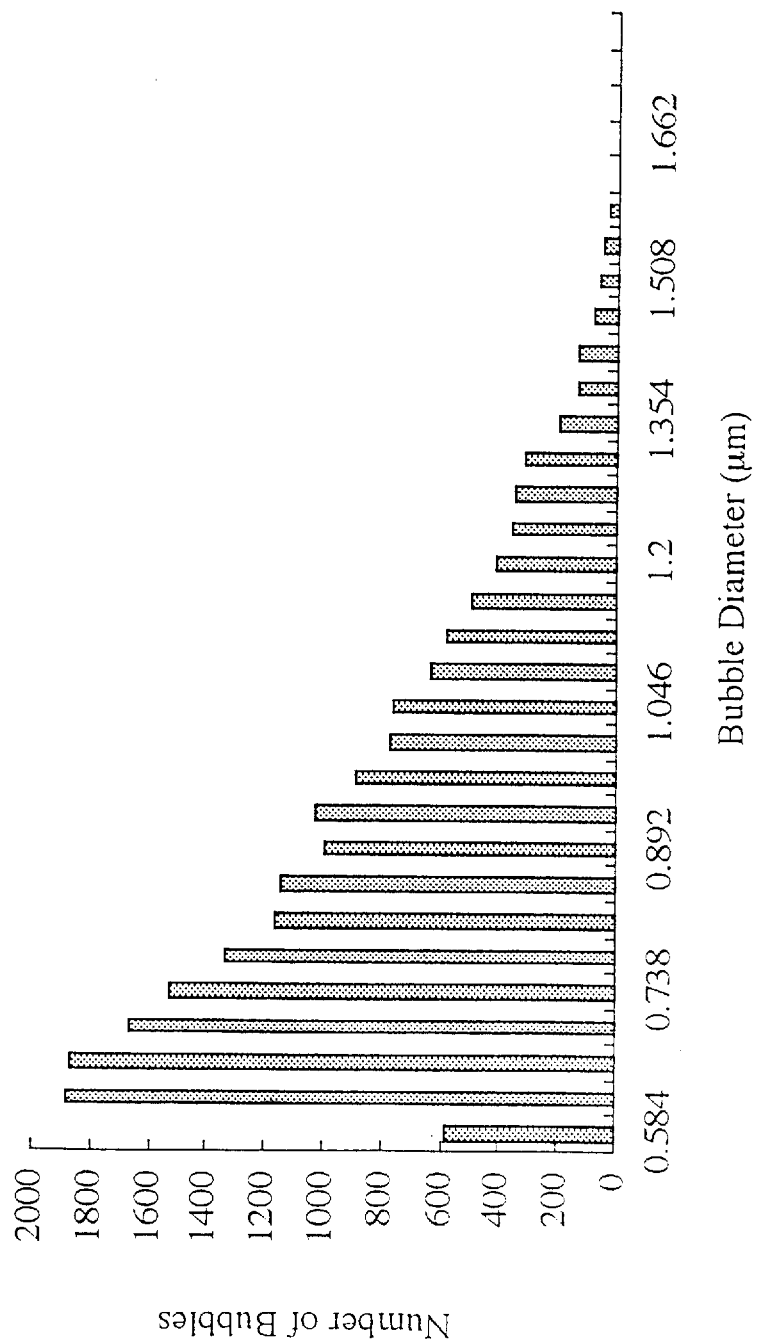
FIG. 2 is a histogram graphically illustrating a typical particle size distribution of stable microbubbles obtained in accordance with the method of the present invention, as determined by Coulter multisizer. The mean particle diameter is measured to be 0.910 μm. 99% of microbubbles less than 1.346 μm.
Figure 3:
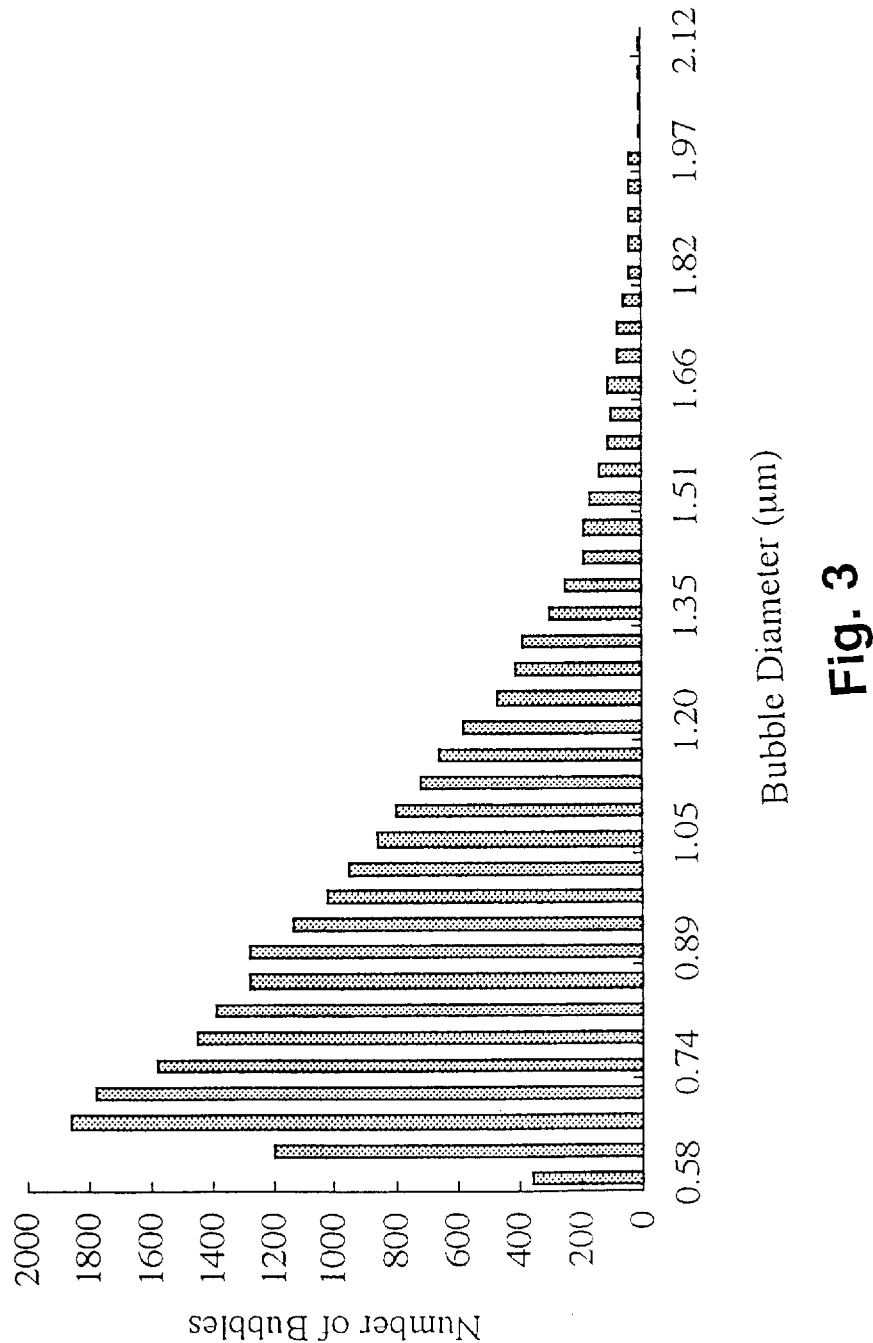
FIG. 3 is a histogram graphically illustrating the particle size distribution of stable microbubbles of which the size is greater than that in FIG. 1. The mean particle diameter is 1.030 μm and 99% of particle size is less than 3.345 μm. The different in mean size is obtained intentionally by the method described in this invention.
Figure 4:
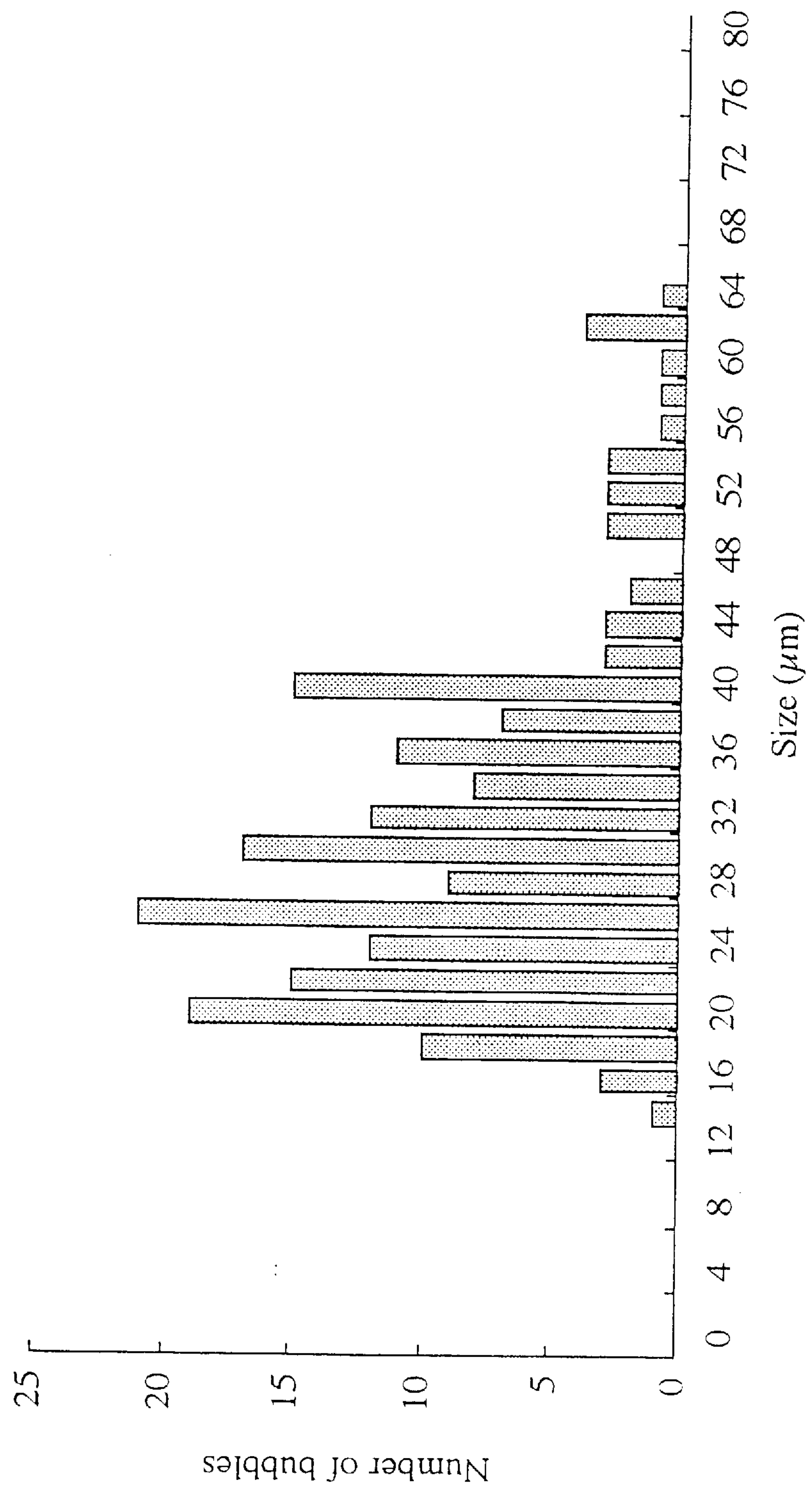
FIG. 4 is a histogram graphically illustrating the particle size distribution of microbubbles prepared in this invention according to example 4 mentioned below.
Figure 5A:
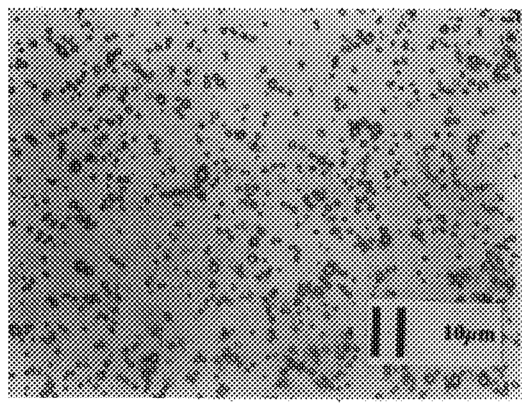
FIG. 5A: the photograph of the bubble sample mentioned in FIG. 2 shown above.
Figure 5B:
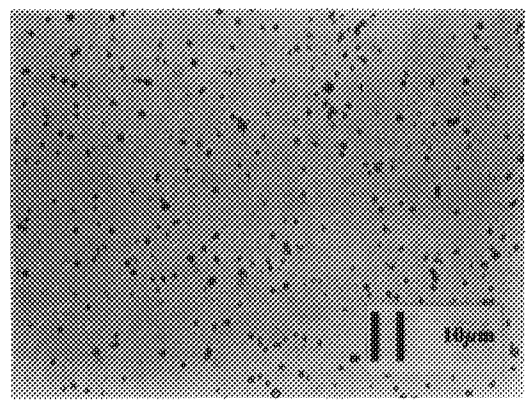
FIG. 5B: the photograph of the bubble sample mentioned in FIG. 1 shown above.

This invention is directed to producing microbubble type contrast agent which is (i) biocompatiable or biodegradable.
(ii) small enough to pass through lungs capillary beds.
(iii) ultrasonically echogenic.
(iv) stable for storage at room condition.
(v) quantitatively reproducible.

In this invention, a method is introduced to produce microbubbles of size range as small as from under 0.5 μm to 5 μm which can exist under room temperature storage for at least 6 months. The basic components in this invention include (1) Homogenizer of which (a) the shaft can rotate at a speed (from 0 to above 20,000 rpm) and it can rapidly introduce bubbles into the solution in which the shaft is immersed.

(b) has a hole on the shaft which is capable of sucking air or gases from the outside environment. After the air is sucked from the outside, by the high-speed rotating motion, the air is rapidly introduced into the solution.

(c) the basic function is to make particles smaller by mechanical meaning.

In this invention, a new function of the homogenizer is introduced that the homogenizer can be used to produce microbubbles of a smaller size range from less than 0.5 μm to 5 μm.

Homogenizer is commercially available machine that can be available from Nition, Kinematica, Hitachi, Homogenizer Polytron, or IKA Ultra-Turrax or other companies.

Also there are other kinds of machines which are commercially available that can be used to make microbubbles, such as Vibro Mixer, Poem Labo of Reica.

Also bubbles can also be produced by other kinds of equipment such as atomizer.

(2) a member chosen from the group of surfactants consisting of Sodium Salt of saturated carboxylic acids containing from about 10 to about 18 carbon atoms. Examples include Sodium Stearate, Sodium Laurate, Sodium Oleate . . . etc.

(3) Another material chosen from the group of surfactants which is currently used as producing bubbles which includes (i) Saponin (ii) Stearic acid (iii) Phloxine (iv) Crystal Violet (v) Polyvinyl alcohol (vi) Sodium Laurate which is capable of producing and stabilizing microbubbles produced from the surfactant described above in (2) temporarily and the other function is to slow down the rapid reaction between the surfactant mentioned above in (2) and the stabilizer that will be described immediately in (4) below.

(4) a member chosen from the group of reagents which can change the nature of the surface of the microbubbles produced from the procedure combining (1) (2) and (3) above. These are the salts that when dissolved in water, a cation comes out that will have a reaction which the group (2) and (3) mentioned above. Examples of these are Calcium Chloride and Magnesium Chloride.

(5) a separation procedure to enable us to collect different range of size of bubbles according to out interest.

Firstly a mixture is made by admixing solid selected from group (2) and (3) described above Said mixture from group (2) and (3) in the said ratio 1:0.1–1:2.0.

The procedure in producing microbubbles is first taking small amount of surfactant from components (2) and (3) described above and put it into pure water making a 0.1% solution. To distribute the solid surfactant well in the solution and produce concentrated bubble solution, a stepwise homogenizing technique is used. The stepwise homogenizing technique includes three procedures. Firstly, after the mixture produced above is put into the pure water, the solution is homogenized at a low homogenizing speed for a short time and the process is repeated once. A white emulsion is obtained. Then a higher homogenizing speed is then applied to the emulsion for a longer time. An emulsion concentrated with bubbles ranging from less than 1 $\mu$m up to 70 $\mu$m is produced.

By process of separation of bubbles by the use of burette (which is a long glass tube with a stopcock at the bottom), small size bubbles can be obtained. After the concentrated bubble solution is produced, the emulsion is put into a burette. Since larger size bubbles will rise up the burette faster than smaller bubbles. So that after storing the bubbles in the burette for a period of time, the microbubbles at the bottom of the burette will be only small size bubbles. Only bubbles at the bottom of the burette are collected. The storage in burette can be in 4° C. or 24° C. or at room condition. The microbubbles that are larger than required are discarded.

After the microbubble emulsion is collected from the burette, another material is used which can change the chemical nature of the coating of microbubbles is added to the microbubble emulsion. Small amount of 0.2–30% solution of the chemical described in group (4) is added to the emulsion collected. These chemicals can be said to be a stabilizer of microbubbles produced. By these processes, stabilized small microbubbles which are of size from less than 1 to 5 $\mu$m are formed. The bubbles can exist for at least 9 months after production.

Particle size analysis is determined by electroimpedance-sensed volumetric sizing multisizer. In this invention, microbubbles of number in the order of $1\times10^9$ per milliliter with the mean size less than 1 $\mu$m is produced. In addition, 99% of the microbubbles produced is less than 3 $\mu$m in diameter.

Also by this method of collecting of microbubbles, we can make microbubbles of the range from less than 1 $\mu$m to 4.5 $\mu$m and from less than 1 $\mu$m to 16 $\mu$m in diameter. By controlling the homogenizing time and speed and the materials used, we also can control microbubbles of the size range between 0.1 and 200 $\mu$m in diameter.

EXAMPLE 1

This example illustrates the preparation of surfactant mixture. A dry powdery surfactant mixture was prepared in accordance with the present invention by admixing Sodium Stearate and Saponin in the ratio 1:0.1–1:1.

EXAMPLE 2

This example illustrates the method of preparation of stable gas-in-liquid emulsion. 80 mg of surfactant mixture as produced from example 1 is used. The solution is first homogenized at a 5,000 rpm for 1 minutes and wait for 2 minutes for dispersion and the process is repeated once. Then the solution is homogenized at a 10,000 rpm to produce large amount of bubbles.

Separation method

The emulsion from example 1 is put into a 25 ml burette. Then after putting into the burette into a refrigerator at 4° C. for 1 hour, 2.5 ml of bubble solution is taken from the bottom of the burette.

Stabilization

Then 200 $\mu$l of 3% $CaCl_2$ solution is put into the 2.5 ml of microbubble solution. The mean size of microbubbles is measured to be 0.971 $\mu$m and the bubble number is measured to $1.3668\times10^9$ per millimeter. 99% of microbubbles is less than the size 2.2708 $\mu$m.

EXAMPLE 3

This example illustrates the significance of using the burette as the method to collect different mean size of microbubbles. The microbubbles is collected from the level 2.5 ml to 5 ml from the burette. The mean size is measured to be 1.0122 $\mu$m and the bubble number is measured to be $1.697\times10^9$ per millimeter. 99% of bubble is less than size 3.578 $\mu$m in diameter.

EXAMPLE 4

This example illustrates the effect of different homogenizer speed and homogenizing time on the size of microbubbles produced. The surfactant mixture is produced as in example 1 and example 2. 80 mg of surfactant mixture is put into 80 ml of water and the solution is homogenized first at a speed of 5,000 rpm for 30 seconds and then wait for 1 and a half minutes and then the solution is homogenized as a 7,500 for 10 seconds. 15 μm to 65 μm of microbubbles is produced. Also by further decreasing the homogenizer speed, the size of microbubbles produced can be up to 200 μm.

EXAMPLE 5

This example illustrate about the effect of toxicity of microbubbles. Bubbles are manufactured as illustrated in example 1 and example 2. 18 Wistar rats with 9 male and 9 female rats ranging from 300 to 400 g are divided into three groups to receive three kinds of dose including (i) 1 ml microbubble solution per 250 g weight of rat.
(ii) 0.5 ml microbubble solution per 250 g weight of rat.
(iii) 0.2 ml microbubble solution per 250 g weight of rat.

These three kinds of dose are injected into the 18 rats everyday for 14 days. No rat died after injection for 14 days, and there is no observable abnormality in the behavior of all the rats. This phenomenon illustrates that the microbubbles have no fatal toxicity.

What is claimed is:

1. A method for preparing an imaging agent for ultrasound comprising the steps of:

A) obtaining an aqueous surfactant mixture for producing a stable microbubble solution containing:
   (a) at least one first surfactant selected from the group consisting of sodium stearate, sodium palmitate or mixtures thereof, and
   (b) at least one second surfactant selected from the group consisting of saponin;

B) forming bubbles in the aqueous surfactant mixture by subjecting the aqueous surfactant mixture to a high speed mixing using a machine having a shaft rotating at a high rotational speed from 5,000 to over 20,000 rpm, and at the same time, introducing gas into the aqueous surfactant mixture, thereby producing a microbubble solution comprising a dispersion of microbubbles of sizes from under 1 μm to over 80 μm;

C) pouring the microbubble solution into a tube with a stopcock at the bottom and leaving the tube standing a period of time;

D) collecting the microbubble solution from the bottom of the tube; and

E) stabilizing the microbubble solution by adding a stabilizing solution containing calcium chloride or magnesium chloride to the collected microbubble solution in order to change the nature of the surface of the microbubbles.

2. The method of claim 1, in which the size of the microbubbles can be varied in accordance with homogenizing speed and time.

3. The method of claim 1, in which different range of size of microbubbles can be collected.

4. The method according to claim 1, wherein the machine used is a homogenizer or a Vibro Mixer.

5. The method according to claim 1, wherein the aqueous surfactant mixture has a weight ratio of the first surfactant to the second surfactant in the range of 1:0.05–1:2.

6. The method according to claim 1, wherein the aqueous surfactant mixture has a weight ratio of the first surfactant to the second surfactant equal to 1 to 1.

7. The method according to claim 1, wherein the aqueous surfactant mixture consists essentially of sodium stearate and saponin.

8. The method according to claim 1, wherein the aqueous surfactant mixture is formed by dissolving 80 mg of the first and second surfactants in 80 ml of water.

9. The method according to claim 1, wherein the bubble forming step B comprises a low speed mixing of the aqueous surfactant mixture prior to subjecting the aqueous surfactant mixture to a high speed of rotation to produce high concentration of microbubble solution.

10. The method according to claim 9, further comprising the step of subjecting the aqueous surfactant mixture to a second low speed mixing process before the high speed mixing process.

11. The method according to claim 1, wherein said stabilized microbubble solution is formed with substantially 99% of the microbubbles having diameters less than 3 μm.

12. The method according to claim 1, wherein said stabilized microbubble solution occurs when the concentration of the microbubble is more than $1\times10^9$ microspheres per milliliter.

13. The method according to claim 1, wherein the stabilized microbubble solution produced can be stable for over 9 months at room condition.

* * * * *